Figure 1:
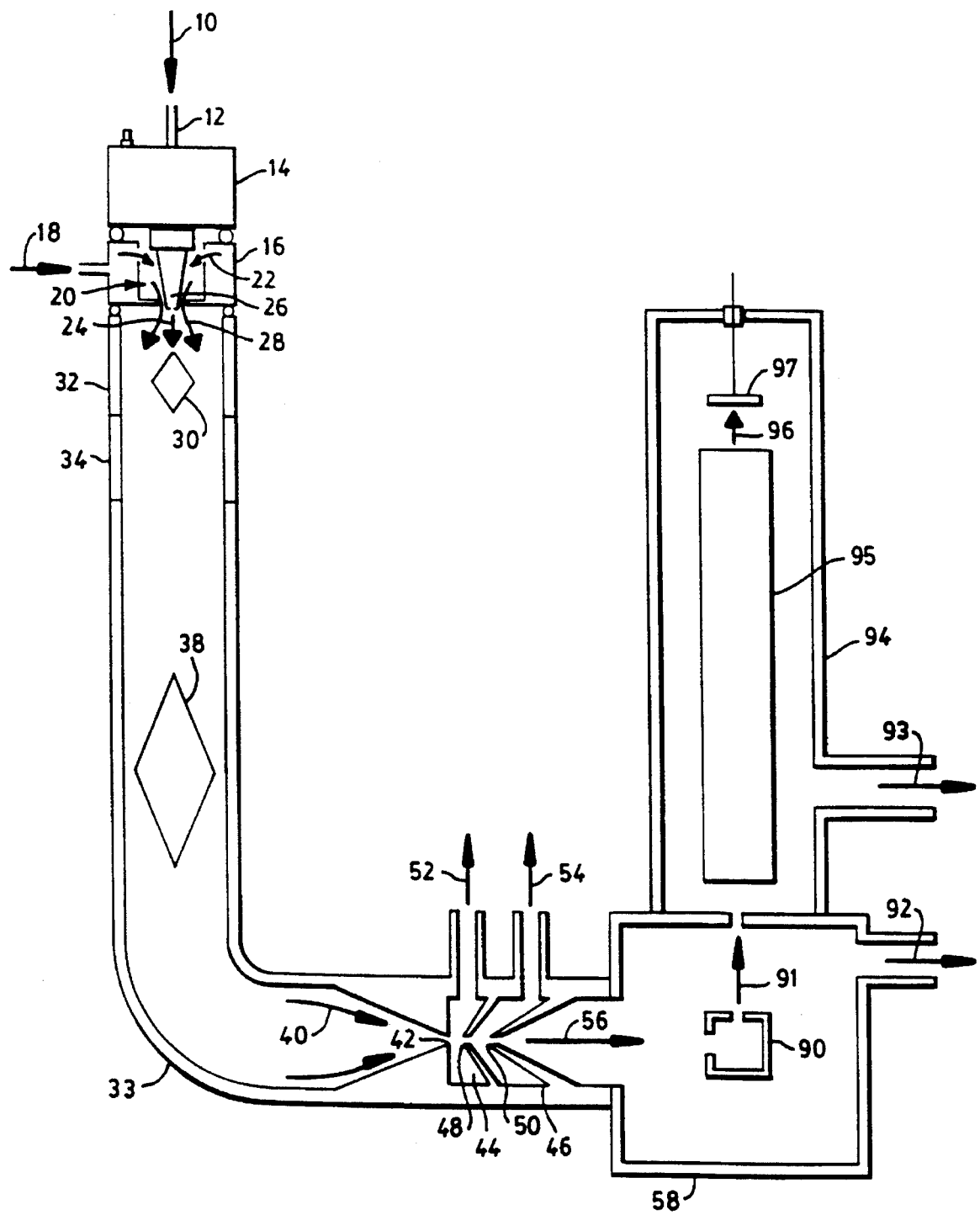

United States Patent [19]

Jarrell et al.

[11] Patent Number: 5,526,682
[45] Date of Patent: Jun. 18, 1996

[54] METHOD AND APPARATUS FOR ANALYZING SAMPLE SOLUTIONS

[75] Inventors: Joseph A. Jarrell, Newton Highlands, Mass.; Michael Tomany, Thompson, Conn.; Stephen C. Gabeler, Sudbury, Mass.

[73] Assignee: Waters Investments Limited, Wilmington, Del.

[21] Appl. No.: 245,398

[22] Filed: May 18, 1994

Related U.S. Application Data

[63] Continuation of Ser. No. 987,863, Dec. 9, 1992, abandoned, which is a continuation-in-part of Ser. No. 694,703, May 2, 1991, abandoned.

[51] Int. Cl.$^6$ .............................. G01N 30/72; G01N 1/00
[52] U.S. Cl. .................. 73/61.55; 73/61.56; 73/863.21; 250/288; 250/424; 250/425
[58] Field of Search .................................... 73/53.01, 61.41, 73/61.43, 61.44, 61.52, 61.56, 61.58, 61.59, 61.71, 61.61, 863.11, 863.12, 863.21, 864.81, 61.55; 250/288, 304, 425, 281, 424

[56] References Cited

U.S. PATENT DOCUMENTS

| | | | |
|---|---|---|---|
| 4,570,068 | 2/1986 | Sakairi et al. | 250/288 |
| 4,670,137 | 6/1987 | Koseki et al. | 73/61.77 |
| 4,861,988 | 8/1989 | Henion et al. | 250/288 |
| 4,958,529 | 9/1990 | Vestal | 73/864.81 |
| 4,977,785 | 12/1990 | Willoughby et al. | 73/863.12 |
| 4,980,057 | 12/1990 | Dorn et al. | 250/288 |
| 4,999,493 | 3/1991 | Allen et al. | 250/288 |
| 5,170,052 | 12/1992 | Kuto | 250/288 |

*Primary Examiner*—Hezron E. Williams
*Assistant Examiner*—Michael J. Brock
*Attorney, Agent, or Firm*—Huw R. Jones; Andrew T. Karnakis

[57] ABSTRACT

A system and process for analyzing a liquid sample is disclosed which includes an ultrasonic nebulizer capable of vibrating at a frequency between about 50 Khz and 760 Khz for converting the liquid sample to a liquid aerosol. The liquid aerosol is heated at a pressure of at least atmospheric pressure to evaporate solvent in the aerosol and to form a solid aerosol. The solid aerosol is separated from the evaporate solvent and the solid aerosol is directed into an electron impact ionizer and a mass spectrometer where it is analyzed.

5 Claims, 5 Drawing Sheets

METHOD AND APPARATUS FOR ANALYZING SAMPLE SOLUTIONS

REFERENCE TO RELATED APPLICATION

This is a continuation of application Ser. No. 07/987,863 filed on Dec. 9, 1992, now abandoned, which in turn is a continuation-in-part of application Ser. No. 07/694,703, filed May 2, 1991, now abandoned.

BACKGROUND OF THE INVENTION

This invention relates to a method and apparatus for analyzing solutes in a sample solution by nebulizing the solution and detecting the solute in the nebulized particles. More particularly, this invention relates to the use of a nebulizer which utilizes ultrasonic excitation to form a standing wave on a liquid surface. The particle size distribution of the nebulized liquid is relatively insensitive to liquid density and liquid surface tension.

At the present time apparatus are available for nebulizing a sample solution such as a liquid stream effluent from a liquid chromatography separation step and subsequently analyzing the nebulized liquid such as by mass spectrometry. Presently available means for analyzing small sample solutions include infrared spectroscopy and mass spectrometry. In electron impact mass spectrometry procedures, for example, the mass spectra of a sample is generated by ionizing the sample, determining the mass spectrum of the ionized sample and comparing the generated mass spectrum with reference mass spectra to determine the identity of the sample. In order to promote accuracy of the procedure, only the mass spectrum of one species should be generated at a given time.

In a liquid chromatograph, a stream of solvent, containing a mixture of chemical species in solution, is passed at elevated pressure through a chromatographic column. The column is so designed that it separates the mixture, by differential retention on the column, into its component species. The different species then emerge from the column as distinct bands in the solvent stream, separated in time. The liquid chromatograph provides therefore, an ideal device for the introduction into a mass spectrometer of single species, separated from initially complex mixtures.

In order for the species emerging from the column to be introduced into a mass spectrometer, removal of solvent from the dissolved species is desirable. The allows the ionization chamber of the mass spectrometer to operate at normal operating pressures (e.g., $10^{-5}$ to $10^{-6}$ torr for electron impact ionization; 1 torr for chemical ionization) and it allows normal ionization modes, such as electron or chemical to be used. Without efficient solvent removal from the species entering the ionization chamber of the mass spectrometer, hybrid and less well characterized mass spectra are produced.

In many systems for interfacing a liquid chromatograph to mass spectrometers, it is necessary to generate aerosols from the liquid chromatography liquid effluent to produce liquid particles having a relatively uniform size and within a count mean diameter of between about 5 and 30 microns. If the particles are to small, it is difficult to separate the solid particles produced therefrom after the solvent evaporates from the vaporous solvent. If the particles are too large, the solvent is incompletely evaporated and the force of gravity will divert them from their intended path. The count mean diameter is defined as the particle size within the aerosol for which half the total number of aerosol particles is larger and the other half is smaller.

An additional problem in forming aerosols from the effluent stream from a liquid chromatography (LC) process is that the LC process must be capable of accommodating a wide variety of solvents so that a wide variety of solutes having different solubility characteristics can be processed. These solvents have different density and surface tension characteristics which affect liquid particle size of an aerosol formed under a given set of energy conditions.

It has been proposed in U.S. Pat. Nos. 4,629.478; 4,687, 929 and 4,762,995 to utilize a nebulizer for producing aerosol particles from an LC column for subsequent introduction into a mass spectrometer. The nebulizer forms liquid particles from a jet of liquid issuing from a nozzle orifice. The diameter of the orifice and the velocity of the jet are controlled so that the jet breaks up into monodisperse liquid particles. Unfortunately, the performance of this nebulizer is dependent upon the density, viscosity and surface tension characteristics of the liquid jet and it is difficult to produce consistently monodisperse aerosols from the variety of solvents utilized in LC. These nebulizers are unstable and require frequent adjustment. An alternative system is disclosed in U.S. Pat. No. 4,383,171 , although no specific nebulizer is disclosed.

An alternative means for forming aerosols from an LC effluent stream is disclosed in UK Patent Application 2,203, 241A which utilizes a capillary tube to form a liquid jet in combination with heating means to heat liquid particles formed from the jet in order to vaporize the solvent in the particles.

Nebulizer devices also are utilized to form aerosols in a wide variety of applications, particularly in applications where liquid fuels are to be burned. It is more efficient to form aerosols from the liquid fuel to increase the surface area of the fuel so as to effect more complete combination. Generally, these nebulizers are utilized with a petroleum fraction having relatively uniform density and surface tension characteristics. Examples of such nebulizers are disclosed in U.S. Pat. Nos. 4,153,201; 4,352,459 and 4,723, 708.

As disclosed in U.S. Pat. No. 4,980,057 and in the 38th ASMS Conference on Mass Spectrometry and Allied Products, pages 1222–1223, a system is provided for analyzing sample solutions comprising an ultrasonic nebulizer and a mass spectrometer. According to this patent, the desolvation chamber adjacent the nebulizer must be operated at subatmospheric pressures. Such operation causes "bumping" or surging of solvent which can disrupt the nebulizer operation. In order to eliminate "bumping", the liquid sample is introduced into the nebulizer orthogonally to the tip of the ultrasonic horn in the nebulizer and orthogonally to a helium stream which is introduced axially into the nebulizer through an axial conduit within the ultrasonic horn. Thus, the helium stream is positioned within the liquid sample stream and the liquid sample stream is fractured to form an aerosol by a combination of pneumatic and ultrasonic forces. In this system the liquid sample effluent conduit must be accurately aligned relative to the ultrasonic horn in contrast to introducing the liquid axially through the ultrasonic horn where proper alignment is inherent. During use, the liquid sample effluent conduit will become misaligned which requires periodic adjustment of the conduit's position. In addition, the use of a gas stream to intimately mix with the liquid sample stream rather than enclosing the liquid sample stream is undesirable since this mode of operation increases the probability that the liquid particles will impact with the apparatus wall and will be lost from downstream analysis.

Electron impact ionization is utilized in analytical processes to permit analysis of molecules dissolved in a liquid of varying composition by providing electron impact ionization spectra of the molecules. This is the fundamental goal of all "particle beam" interfaces for coupling liquid streams to mass spectrometers. The primary advantage of such spectra for the analysis or identification of small molecules (less than 1000 Daltons) is that they are highly specific to the molecules from which they are generated and provide a wealth of structural information. In addition, large libraries of such spectra exist such that it is possible to computer search for a match between the spectrum of an unknown compound and spectra in these libraries. These are the same kind of spectra that are produced by traditional coupling of a gas chromatograph to a mass spectrometer. Such spectra are the only kind widely accepted today for the analysis and identification of unknown compounds.

The specificity of such electron impact ionization spectra is a consequence of the fact that ionization occurs at a low pressure (typically less than $10^{-4}$ Torr) and that ionization of an individual molecule results solely from the collision of an energetic electron (energies typically 100–150 eV) with that neutral molecule.

Figure 2:
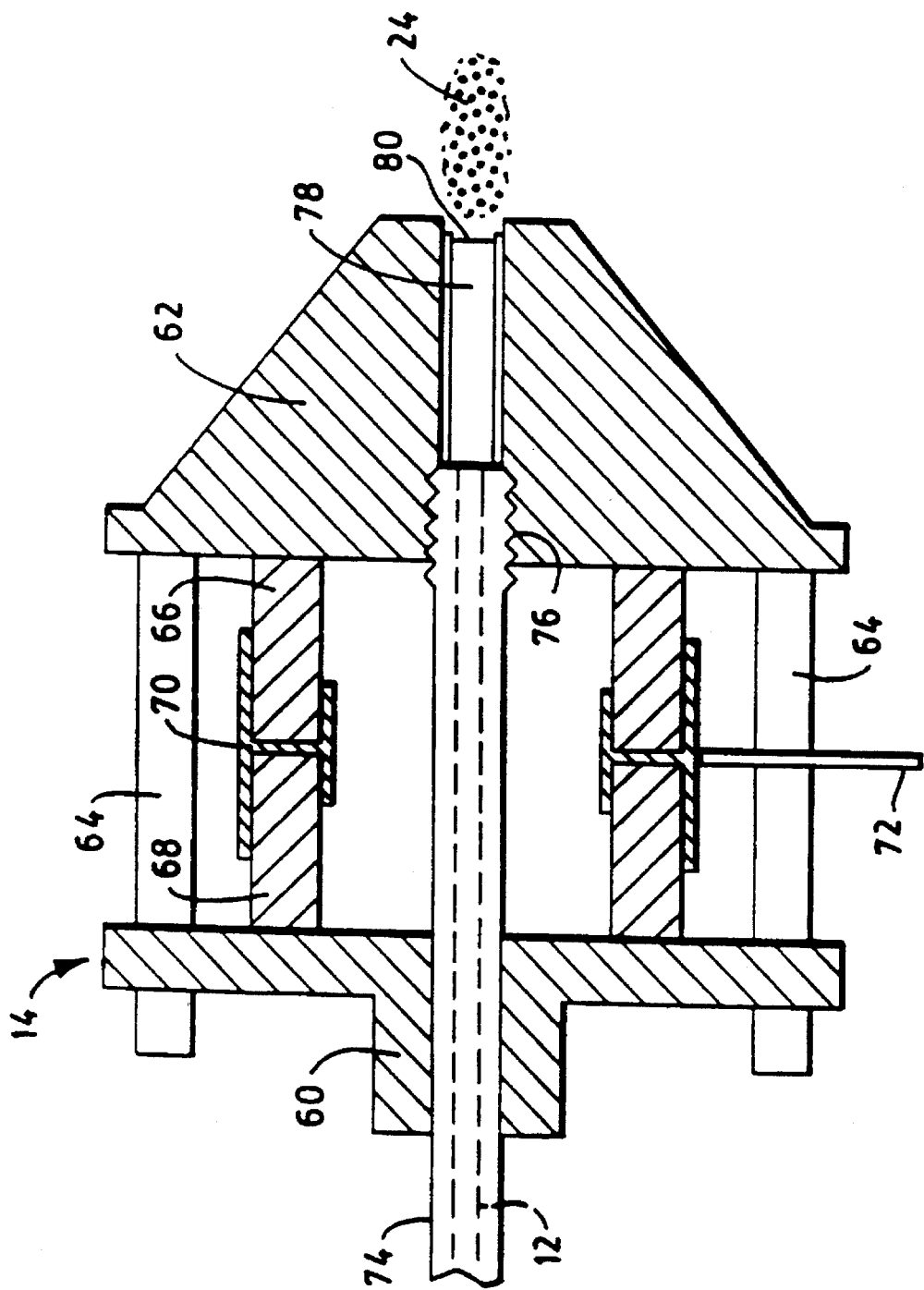

It would be desirable to provide a system for forming an aerosol from the liquid effluent of an LC apparatus, regardless of solvent used in the stream. This would substantially eliminate the need for adjustment of the nebulizer when the LC stream solvent is changed. Such a system would be capable of producing aerosols having a relatively uniform droplet distribution, which in turn could be efficiently desolvated to produce a dry "particle beam" of any solute molecules dissolved in the LC solvent stream such that the electron impact ionization spectra of said solute molecules could be easily and efficiently generated.

SUMMARY OF THE INVENTION

The present invention comprises a system for analyzing the liquid effluent of an LC apparatus which includes an ultrasonic nebulizer to form a aerosol from the effluent, means for desolvating the aerosol droplets and analyzing means. The ultrasonic nebulizer comprises means for delivering the effluent to a small column where ultrasonic vibrations are generated to form capillary waves which are fractured to form an aerosol. The aerosol is heated with a gas stream which encloses the aerosol to vaporize solvent in the aerosol droplets in a desolvation chamber thereby to form dry particles which are directed to an analyzing means which utilizes electron impact ionization to form an ion beam which then is analyzed such as in a mass spectrometer. The desolvation chamber is maintained at a pressure of at least atmospheric pressure. This system has the advantage of relative independence of sensitivity of response to mobile phase composition and flow rate. This independence is achieved without the need for nebulizer optimization as flow rate or composition are varied. In addition this system is operable at flow rates as low as 50 μL/min which is the rate of flow in microbore and capillary liquid chromatography. Furthermore, this system provides electron impact ionization spectra of sample molecules dissolved in a liquid.

BRIEF DESCRIPTION OF THE DRAWINGS

FIG. 1 is a schematic view of the system of this invention.

FIG. 2 is a cross sectional view of an ultrasonic nebulizer which is used in the system of this invention.

FIG. 3 shows the system response to a series of rotenone injections ranging from 2.5 ng to 400 ng.

FIG. 4 is a plot of the data of FIG. 3.

FIG. 5 shows the relative insensitivity of the system of this invention to flow variations.

DESCRIPTION OF SPECIFIC EMBODIMENTS

In the system of this invention, the liquid effluent from a liquid chromatography separation process is directed to an ultrasonic nebulizer as a narrow stream. An ultrasonic nebulizer operates at a frequency above the limit of human hearing (16–20 Khz). In this invention, the ultrasonic nebulizer is operated at a frequency between about 50 and 760 Khz, preferably between about 100 and 140 Khz. If operated above this frequency range the particles are too small to be separated from a gas stream, If operated below this frequency range, the liquid particles are separated by gravity. In comparison to other available nebulizers of the prior art, the function of the ultrasonic nebulizer to produce monodisperse aerosol droplets is relatively insensitive to liquid surface tension, liquid viscosity and liquid density. The aerosol particle size produced with an ultrasonic nebulizer is defined by the expression:

$$CMD=\left(\frac{\gamma}{\rho_L f^2}\right)^{1/3}$$

Wherein γ is the liquid surface tension, ρL. is the liquid density, f is the excitation frequency and CMD is the count mean diameter. As is evident from the above expression the aerosol particle distributions vary only as the ⅓ power of the liquid surface tension and liquid density. Thus, the ultrasonic nebulizer is relatively immune to the need for adjustment or loss of sensitivity as a function of solvent composition. The resulting aerosol is enclosed by a heated gas stream in a desolvation chamber under conditions to confine the aerosol as a stream of particles and to heat the particles to evaporate the solvent and to form solid particles comprising the solute. The desolvation chamber is maintained a a pressure of at least atmospheric pressure, typically about 2–15 psig. or higher. The enclosing gas stream provides the desired pressure in the desolvation chamber and prevents the aerosol from contacting the chamber walls. The evaporated solvent is separated from the solid particles and the solid particles are directed into an analyzing step which includes electron impact ionization mass spectrometry or infrared spectroscopy.

Referring to FIG. 1, an effluent stream 10 from an LC Column (not shown) enters a conduit 12 within an ultrasonic nebulizer 14. The pressure within the desolvation chamber 32 is at atmospheric or superatmospheric. A hot inert gas such as helium enters plenum 16 through conduit 18 and then enters inner plenum 20 through openings 22. The liquid stream is converted to liquid droplets 24 at the exit of nebulizer tip 26 where they contact the hot inert gas exiting from opening 28 which surrounds nebulizer tip 26. The hot inert gas does not serve to form the aerosol but rather serves to heat and enclose the liquid aerosol to evaporate solvent and to minimize contact of the aerosol with the walls of the chamber 32. The solvent in the liquid droplets evaporates to form partially desolvated particles 30 within chamber 32 which can be supplied with windows 34, if desired. Chamber 32 can be provided with a bend 33 which contacts large solvent particles which may be formed intermittently within the nebulizer 14 and are incapable of following the path of the bend 33 due to inertia. The bend 33 is not required but its inclusion comprises a preferred embodiment of this invention. Heat can be provided to the interior of chamber 32 by external heaters (not shown) in order to accelerate solvent vaporization. The partially desolvated particles 30 are converted to solid particles 38 due to solvent evaporation. The desolvated particles are light enough that they are entrained by the gas/solvent vapor flow 40. Gas, solvent vapor, and particles flow out of the desolvation chamber 32 through orifice 42 from which they emerge in the form of a jet. The gas/particle/solvent vapor jet then passes through a series of pumped skimmers 44 and 46. The gas and solvent vapor molecules, having a higher diffusivity, spread out perpendicular to the axis of jet flow faster than do the particles. The jet then passes through orifices 48 and 50 which are in the tips of the skimmers. This process thus enriches the particle density relative to the solvent vapor/gas stream. The excess gas and vapor (and some particles) are pumped out by external pumps (not shown) through port 52 and port 54. Finally the emergent particle beam 56 enters the ionization chamber 58 and into the electron impact ionization region 90 to produce an ion beam 91. A pump out port 92 is provided for ionization chamber 58. The beam 91 enters analyzer chamber 94 and enters mass analyzer 95 to produce analyzed ion beam 96 which impacts ion detector 97. Analyzer chamber 94 is provided with pump out port 93. Referring to FIG. 2, the ultrasonic nebulizer 14 includes a rear section 60 bolted to a nebulizer tip 62 by means of bolts 64. The piezoelectric driving elements 66 and 68 and electrode 70 are positioned between rear section 60 and tip 62 and are connected by electrical lead 72. Tube 74 is provided with a thread 76 which mates with a central thread in tip 62. Tube 74 is provided with a central conduit 12 through which the LC liquid stream passes. The LC liquid stream passes through conduit 78 within tip 62 where it is vibrated to form waves at the liquid surface 80 to produce droplets 24.

The following examples illustrate the present invention and are not intended to limit the same.

EXAMPLE I

This example will be described with reference to FIGS. 1 and 2. A nebulizer having a conduit 78 of about 15 mm in length and a diameter of 0.76 mm was vibrated at a frequency of 120 Khz. A series of rotenone injections of between 2.5 ng and 400 ng in 90/10 v/v of CH3CN/H2O was directed to the nebulizer from a liquid chromatography step at a rate of 0.4 ml/min. The desolvation chamber 32 was maintained at 1 psig. at 66 °C. with a helium flow rate of 2.7 liters/min. The mass spectrometer vacuum system was differentially pumped. The electron impact ionizer 90 was at 242° C. in the chamber 58 at a pressure of $2.0 \times 10^{-5}$ torr. The mass analyzer 95 was in contiguous chamber 94 at a pressure of $6.1 \times 10^{-7}$ torr.

Figure 3:
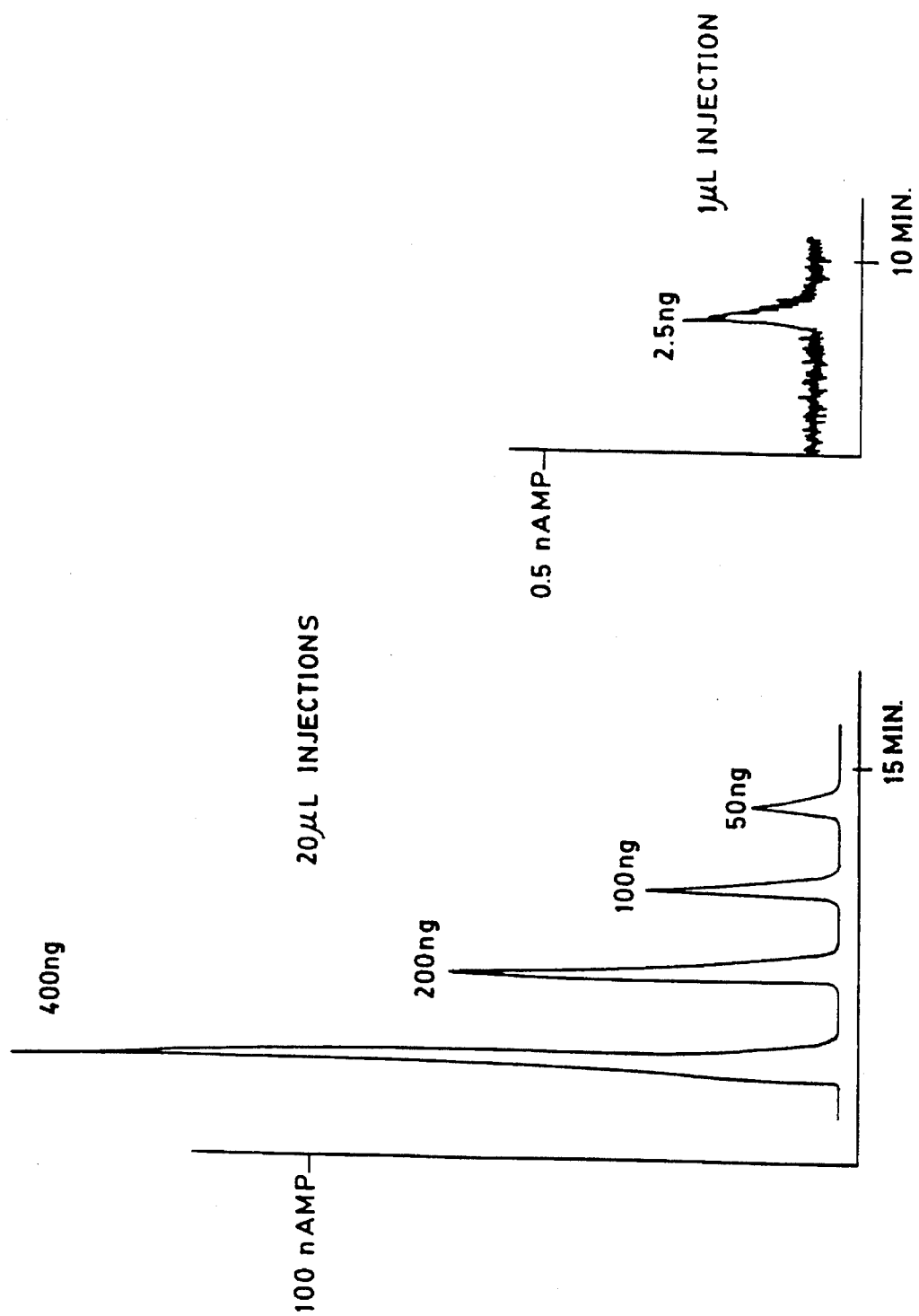
Figure 4:
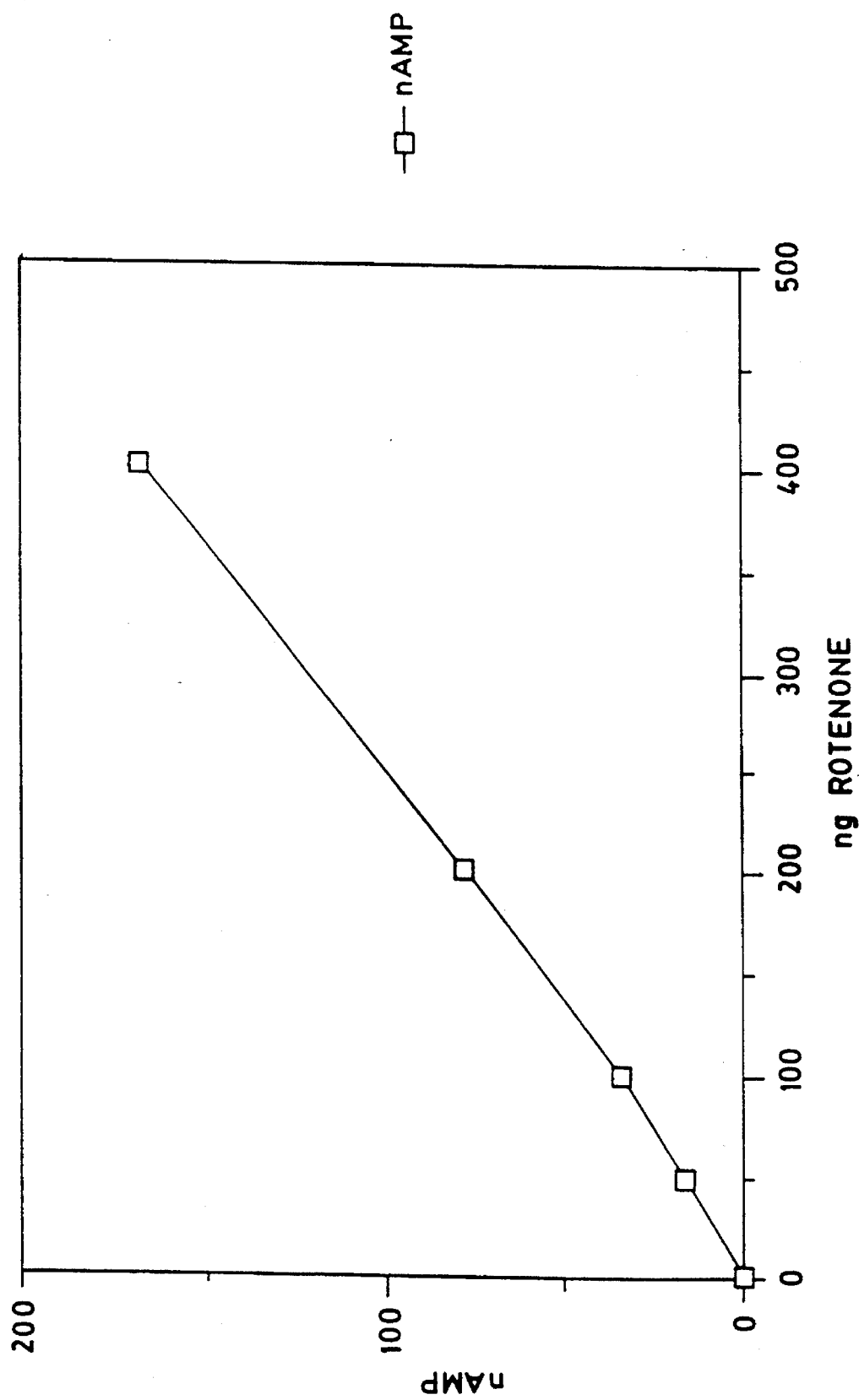

Together, FIGS. 3 and 4 demonstrate the sensitivity and linearity of the system of this invention. The vertical axis on each of these figures is in nanoamperes which is a somewhat arbitrary measure of system response. In practice, however, mass spectrometers are extremely difficult to calibrate absolutely and are therefore virtually always calibrated against external standards. Thus what is important with regard to the sensitivity is the minimum detectable amount with respect to background noise which, from FIGS. 3 and 4 can clearly be less than 1 ng for rotenone.

Figure 5:
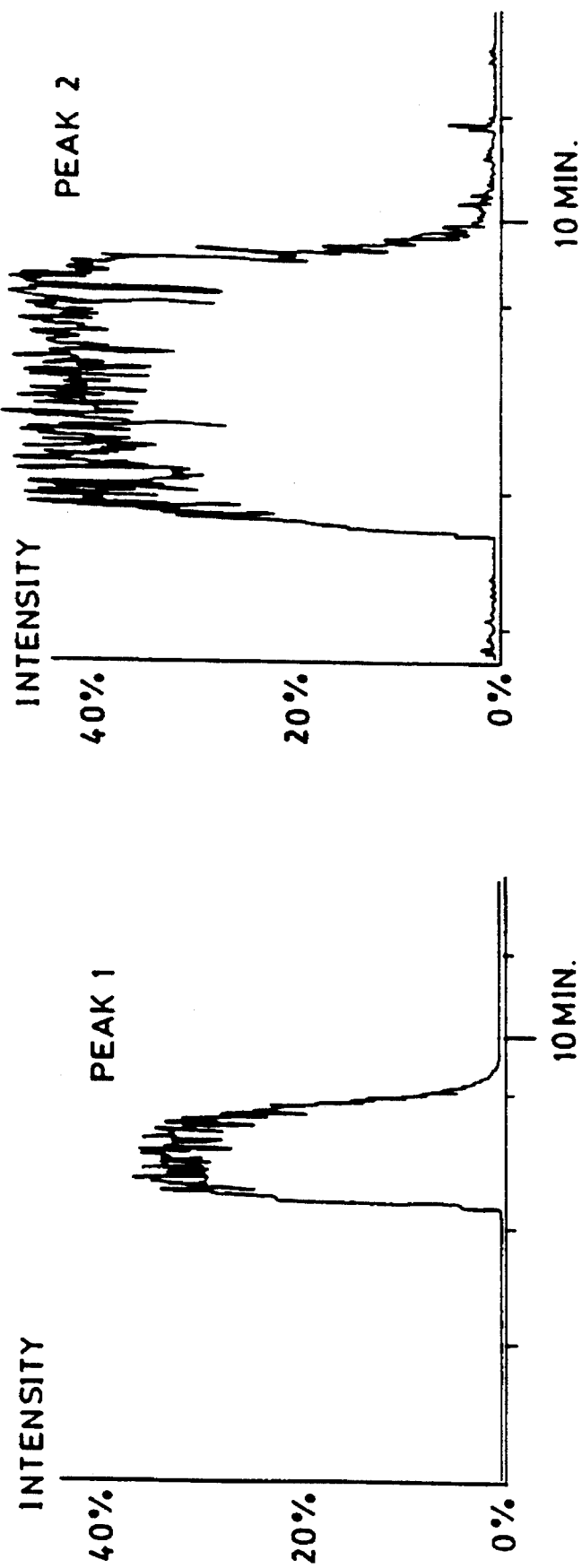

FIG. 5 shows the relative insensitivity of the system to flow variations. Peak 1 is the response to an infusion of 1333 ng/s of linuron at 0.4 ml/min. The desolvation pressure was 2.5 psig and was operated at 88° C. The electron impact ionizer 90 was at 380° C. in the chamber 58 at a pressure of $1.3 \times 10^{-4}$ Torr. The mass analyzer 95 was in contiguous chamber 94 at a pressure of $1.8 \times 10^{-5}$ Torr. Peak 2 is the response to an infusion of 1333 ng/s of linuron at 0.1 ml/min. The response variation is less than 35% despite a 4 times change in flow rate.

We claim:

1. A system for analyzing a liquid sample comprising the effluent of a liquid chromatography column which comprises, an ultrasonic nebulizer capable of vibrating at a frequency between about 50 Khz and 760 khz to form capillary waves in a liquid which are fractured to form a liquid aerosol, conduit means for introducing said liquid sample to be converted to said liquid aerosol, axially into said nebulizer, means for converting said liquid aerosol to a solid aerosol by evaporating solvent of said liquid aerosol with a heated gas stream at a pressure of at least atmospheric pressure which surrounds and contacts said liquid aerosol, a bent chamber for capturing liquid particles larger than said solid aerosol, said chamber positioned after said means for converting said liquid aerosol to a solid aerosol;

skimmer means for separating said solid aerosol from said evaporated solvent, means to ionize constituent molecules of said solid aerosol thus producing an ion beam, and means for analyzing said ion beam.

2. The system of claim 1 wherein said means for analyzing comprises a mass spectrometer.

3. A process for analyzing a liquid sample which comprises:

introducing said sample axially into an ultrasonic nebulizer, vibrating said nebulizer to form capillary waves on the surface of said liquid sample which are fractured to form a liquid aerosol, heating said liquid aerosol to evaporate solvent of said liquid aerosol with a heated gas stream at a pressure of at least atmospheric pressure surrounding and contacting said liquid aerosol to convert said liquid aerosol to a solid aerosol, separating liquid particles larger than said solid aerosol from said solid aerosol, separating evaporated solvent from said solid aerosol with a skimmer, ionizing constituent molecules of said solid aerosol thus producing an ion beam, and analyzing said ion beam.

4. The process of claim 3 wherein said liquid sample is produced in a liquid chromatography column.

5. The process of claim 3 wherein said ion beam is analyzed by mass spectroscopy.

* * * * *